United States Patent
Liu et al.

(10) Patent No.: US 8,790,861 B2
(45) Date of Patent: Jul. 29, 2014

(54) CYCLOALIPHATIC MONOMER, POLYMER COMPRISING THE SAME, AND PHOTORESIST COMPOSITION COMPRISING THE POLYMER

(71) Applicant: Rohm and Haas Electronic Materials LLC, Marlborough, MA (US)

(72) Inventors: Cong Liu, Marlborough, MA (US); Mingqi Li, Shrewsbury, MA (US); Cheng-Bai Xu, Southborough, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 13/723,973

(22) Filed: Dec. 21, 2012

(65) Prior Publication Data

US 2013/0171549 A1   Jul. 4, 2013

Related U.S. Application Data

(63) Continuation-in-part of application No. 13/711,175, filed on Dec. 11, 2012.

(60) Provisional application No. 61/582,345, filed on Dec. 31, 2011.

(51) Int. Cl.
| | |
|---|---|
| G03F 7/039 | (2006.01) |
| G03F 7/09 | (2006.01) |
| G03F 7/20 | (2006.01) |
| C07C 69/54 | (2006.01) |
| C08F 20/68 | (2006.01) |

(52) U.S. Cl.
USPC ..... 430/270.1; 430/910; 430/905; 430/271.1; 430/311; 430/326; 430/9; 430/14; 430/18; 526/328; 560/220

(58) Field of Classification Search
None
See application file for complete search history.

(56) References Cited

U.S. PATENT DOCUMENTS

| | | | |
|---|---|---|---|
| 5,968,713 A | 10/1999 | Nozaki et al. | |
| 2001/0044071 A1* | 11/2001 | Hasegawa et al. | 430/270.1 |
| 2007/0275324 A1 | 11/2007 | Allen et al. | |
| 2010/0304295 A1 | 12/2010 | Kinsho et al. | |
| 2011/0269074 A1 | 11/2011 | Aqad et al. | |

FOREIGN PATENT DOCUMENTS

EP   1148044 B1   1/2004

OTHER PUBLICATIONS

U.S. Appl. No. 13/711,175, filed Dec. 11, 2012, "Cycloaliphatic Monomer, Polymer Comprising the Same, and Photoresist Composition Comprising the Polymer"; 22 Pages.

* cited by examiner

*Primary Examiner* — Sin J. Lee
(74) *Attorney, Agent, or Firm* — Cantor Colburn LLP

(57) ABSTRACT

A monomer has the Formula I:

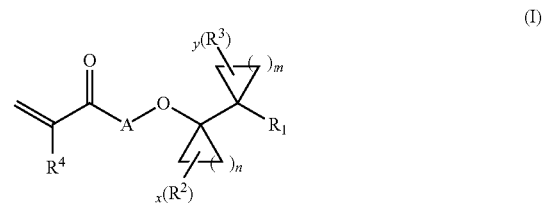

(I)

wherein $R^1$, $R^2$, and $R^3$ are each independently a $C_{1-30}$ monovalent organic group, and $R^1$, $R^2$, and $R^3$ are each independently unsubstituted or include a halogen, nitrile, ether, ester, ketone, alcohol, or a combination comprising at least one of the foregoing functional groups; $R^4$ includes H, F, $C_{1-4}$ alkyl, or $C_{1-4}$ fluoroalkyl; A is a single bond or a divalent linker group, wherein A is unsubstituted or substituted to include a halogen, nitrile, ether, ester, ketone, alcohol, or a combination comprising at least one of the foregoing functional groups; m and n are each independently an integer of 1 to 8; and x is 0 to 2n+2, and y is 0 to 2m+2.

20 Claims, No Drawings

CYCLOALIPHATIC MONOMER, POLYMER COMPRISING THE SAME, AND PHOTORESIST COMPOSITION COMPRISING THE POLYMER

CROSS REFERENCE TO RELATED APPLICATIONS

This application claims the benefit of U.S. Patent Application Ser. No. 61/582,345, filed Dec. 31, 2011, and U.S. patent application Ser. No. 13/711,175, filed Dec. 11, 2012, which are incorporated by reference herein in its entirety.

BACKGROUND

Improved photolithographic technologies based on short wavelength radiation (e.g., as generated by an ArF excimer laser operating at 193 nm), or other such short wavelength sources, are useful in the pursuit of ever faster and more efficient semiconductor devices by increasing device density of an integrated circuit. Photoresist materials useful in such short wavelength applications include chemical amplification-type radiation-sensitive resin compositions, which rely on the efficient interaction of a resin component having an acid labile functional group, and a photoacid generator that generates an acid upon irradiation.

The requisite properties for photoresist materials useful for ArF excimer laser lithographies include transparency (i.e., low optical density) at 193 nm, as well as high etch resistance, conveyed by high carbon density and polycyclic ring structures. Useful photoresist platform resins include those based on a poly(meth)acrylate-based backbone and a carboxylic acid moiety protected with a bulky tertiary alkyl group, which is highly transparent at 193 nm. The efficiency of deprotecting (also referred to herein as "deblocking") the carboxylic acid directly correlates with the contrast and resolution.

A variety of different (meth)acrylate based monomers, having tertiary ester groups which are sensitive to acid, are known. For example, U.S. Patent Application Publication No. 2007/0275324 A1 discloses (meth)acrylate esters based on cycloalkyl moieties having a tertiary center in which the ester oxygen attaches to a tertiary alkyl ring carbon atom having another alkyl or cycloalkyl substituent at the same center (i.e., to make a quaternary center). Polymers prepared using these monomers can provide contrast in a photoresist.

However, as the critical dimension (CD) of semiconductor devices shrinks, still higher resolution photoresists which provide narrow CD control are required for manufacturing of devices at or below the 45 nm device design node.

STATEMENT OF INVENTION

The above and other problems of the prior art may be overcome by a monomer having the Formula I:

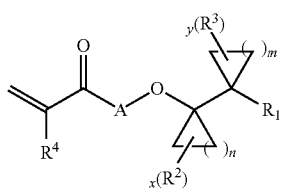

(I)

wherein $R^1$, $R^2$, and $R^3$ are each independently a $C_{1-30}$ monovalent organic group, and $R^1$, $R^2$, and $R^3$ are each independently unsubstituted or include a halogen, nitrile, ether, ester, ketone, alcohol, or a combination comprising at least one of the foregoing functional groups; $R^4$ includes H, F, $C_{1-4}$ alkyl, or $C_{1-4}$ fluoroalkyl; A is a single bond or a divalent linker group, wherein A is unsubstituted or substituted to include a halogen, nitrile, ether, ester, ketone, alcohol, or a combination comprising at least one of the foregoing functional groups; m and n are each independently an integer of 1 to 8; and x is 0 to 2n+2, and y is 0 to 2 m+2.

A polymer, comprises the monomer of Formula I.

A photoresist composition, comprises the polymer and a photoacid generator.

A coated substrate, comprises: (a) a substrate having one or more layers to be patterned on a surface thereof; and (b) a layer of a photoresist composition over the one or more layers to be patterned.

A patterned layer is formed by patternwise imaging the coated substrate using actinic radiation at 193 nm.

DETAILED DESCRIPTION

Disclosed herein is a novel acid-deprotectable (meth) acrylic acid-type monomer suited for use in ArF immersion lithography. As used herein, "(meth)acrylate" means acrylate or methacrylate or a combination comprising at least one of these polymerizable groups. The monomer is a polymerizable, unsaturated ester monomer (e.g., a (meth)acrylate-based tertiary cycloaliphatic monomer) with a tertiary polycyclic leaving group comprising a core ring structure of two cycloaliphatic rings connected by a sigma (σ) bond to form a tertiary center on one ring and a quaternary center on the other. The ester is connected via the tertiary center (thus forming a second quaternary center). The monomer can be used to prepare a polymer for a chemically amplified photoresist composition which exhibits high resolution and etch resistance with ArF photolithography. A patterned layer, and a patterning process for forming a relief pattern using the photoresist composition are also disclosed.

The acid-deprotectable monomer has the Formula I:

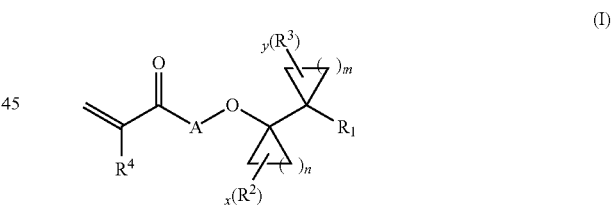

(I)

wherein $R^1$, $R^2$, and $R^3$ are each independently a $C_{1-30}$ monovalent organic group. Substituent groups may be included on one of these monovalent organic groups. $R^1$, $R^2$, and $R^3$ are each therefore independently unsubstituted or include a halogen, nitrile, ether, ester, ketone, alcohol, or a combination comprising at least one of the foregoing functional groups. Preferably, $R^1$, $R^2$, and $R^3$ are each independently $C_{1-10}$ alkyl, $C_{1-10}$ fluoroalkyl, $C_{1-10}$ alkoxy, $C_{1-10}$ fluoroalkoxy, $C_{1-10}$ alkanol, or a combination comprising at least one of the foregoing. Exemplary groups $R^1$, $R^2$, and $R^3$ include, methyl, ethyl, trifluoromethyl, 2,2,2-trifluoroethyl, 2-hydroxyethyl, or a combination comprising at least one of the foregoing.

As used throughout the specification and unless otherwise specified, "substituted" means having a substituent group including —OH, —SH, —CN, halogens including F, Cl, Br, or I, carboxylic acid, carboxylate, $C_{1-10}$ alkyl, $C_{3-10}$ cycloalkyl, $C_{6-10}$ aryl, $C_{7-10}$ aralkyl, $C_{1-10}$ alkyl, $C_{1-10}$ fluoroalkyl, $C_{3-10}$ fluorocycloalkyl, $C_{6-40}$-fluoroaryl, $C_{7-40}$-fluoroaralkyl, $C_{1-10}$ alkyl, $C_{1-10}$ alkoxy, $C_{3-10}$ cycloalkoxy, $C_{6-10}$ aryloxy, $C_{1-10}$alkyl, a $C_{2-10}$ ester-containing group, a $C_{1-10}$ amide-containing group, a $C_{2-10}$ imide-containing group, a $C_{3-10}$ lactone-containing group, a $C_{3-10}$ lactam-containing group, a $C_{2-10}$ anhydride-containing group, or a combination comprising at least one of the foregoing.

Also in Formula I, $R^4$ includes H, F, $C_{1-4}$ alkyl, or $C_{1-4}$ fluoroalkyl. Exemplary groups $R^4$ include H, F, methyl, or trifluoromethyl. It will be appreciated that where $R^4$ is H, the polymerizable portion is an acrylate, and where $R^4$ is $CH_3$, the polymerizable portion is a methacrylate.

A is a single bond or a divalent linker group that may be unsubstituted or include wherein A is unsubstituted or substituted to include a halogen, nitrile, ether, ester, ketone, alcohol, or a combination comprising at least one of the foregoing functional groups. A is preferably a straight or branched $C_{1-10}$ organic group including one or more of the foregoing functional groups. An exemplary group A includes —O—$CH_2$(C=O)—.

Also in Formula I, m and n are each independently an integer of 1 to 8. Further, x is 0 to 2n+2, and y is 0 to 2 m+2. It will be understood that where the variables x and y, which define the number of groups $R^2$ and $R^3$, respectively, substituted on the rings, are less than the maximum possible number for these variables, the vacant valencies on the ring are filled by hydrogen atoms. Preferably for Formula I, m and n are independently 3 or 4, and x and y are independently an integer of from 0 to 2. In an example, for Formula I, when $R^1$ is methyl or ethyl, m and n are each 3, and x and y are each 0.

An exemplary monomer is believed to eliminate by the following mechanism shown in reaction scheme 1. After acid-catalyzed elimination within the resist film, a carbocation forms on the carbon atom to which the polymerizable ester is bonded. Elimination of a proton from the resulting carbocation forms an olefin. Because the carbocation formed in this reaction is more stable, the activation energy of the acid-catalyzed elimination reaction becomes lower, indicating a higher reactivity. The acid-deprotectable monomer has characteristic consecutive quaternary carbon atoms separated by a single bond, and mono-cyclic cycloalkyl groups incorporating the quaternary centers. It is believed that high reactivity is obtained because 1) the quaternary carbon exerts an electron donating effect toward the carbocation, stabilizing the quaternary cation, and 2) the carbocation intermediate formed on the cationic carbon undergoes a rearrangement reaction of alicyclic groups on the quaternary centers, specifically a 1,2-alkyl shift which may occur, so that a further, more stable carbocation may form. Equilibrium between the carbocations is believed to contribute to their stabilization, hence reducing the activation energy of the deprotection reaction.

Reaction Scheme 1

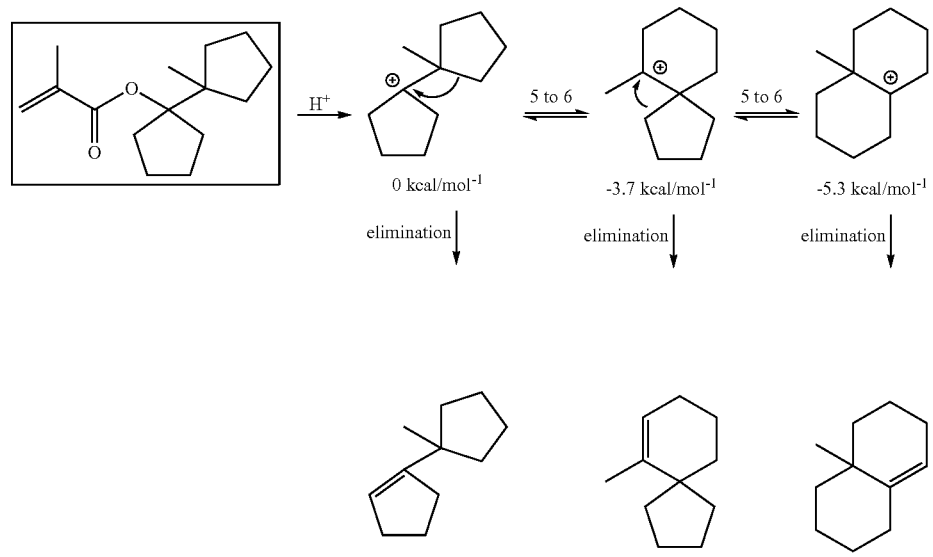

The acid-deprotectable monomer of Formula I is used to prepare a polymer. Polymers prepared from this monomer include homopolymers or copolymers, where such polymers are acid sensitive and provide base-soluble carboxylic acid groups to provide enhanced polymer solubility and contrast. "Copolymer" as used herein means any polymer having two or more different monomeric units, and includes in addition to copolymers having two monomers, terpolymers, tetrapolymers, pentapolymers, etc.

The copolymer includes an additional monomer copolymerizable with the acid-deprotectable monomer of Formula I. Any such additional monomer suitable for forming a 193 nm photoresist polymer may be used, so long as the additional monomer is copolymerizable with the acid-deprotectable monomer described herein, and does not significantly adversely affect the desired properties of the acid-deprotectable monomer. Preferably, the additional monomer is a (meth)acrylate monomer having a base soluble group, a (meth)acrylate monomer having a lactone functional group, an additional (meth)acrylate monomer having an acid-deprotectable group not identical to that of Formula I, or a combination comprising at least one of the foregoing monomers.

Other monomers, such as (meth)acrylate monomers for improving adhesion, etch resistance, etc., may also be included.

Any lactone-containing monomer useful for forming a 193 nm photoresist polymer may be used. Exemplary such lactone-containing monomers copolymerizable with the acid-deprotectable monomer of Formula I may include, but are not limited to:

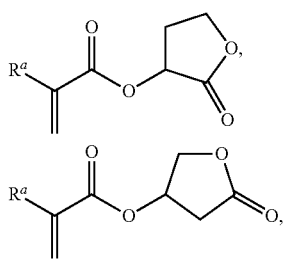

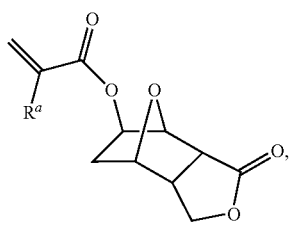

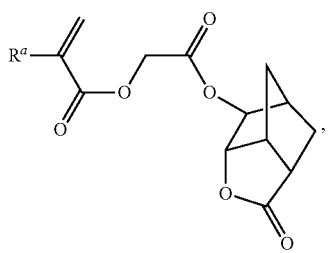

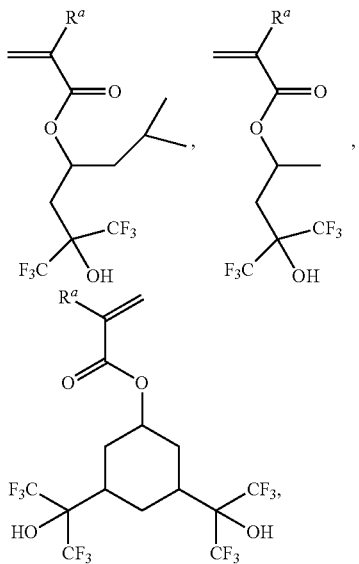

or a combination comprising at least one of the foregoing monomers, wherein $R^a$ is H, F, $C_{1-10}$ alkyl, or $C_{1-10}$ fluoroalkyl.

Any base-soluble monomer useful for forming a 193 nm photoresist polymer may be used. Exemplary base-soluble (meth)acrylate monomers may include, but are not limited to:

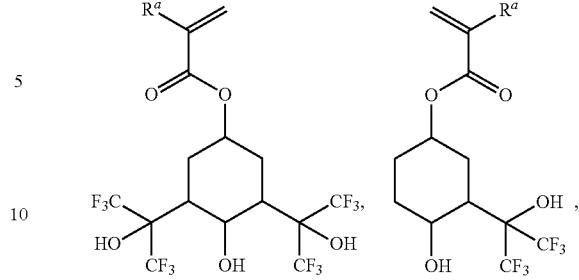

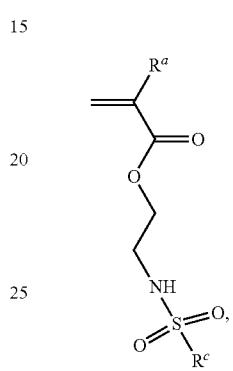

or a combination comprising at least one of the foregoing monomers, wherein $R^a$ is H, F, $C_{1-10}$ alkyl, or $C_{1-10}$ fluoroalkyl, and $R^c$ is a $C_{1-4}$ perfluoroalkyl group.

Any additional acid-deprotectable monomer useful for forming a 193 nm photoresist polymer may also be used. Exemplary acid-deprotectable monomers copolymerizable with the acid-deprotectable monomer of Formula I may include, but are not limited to:

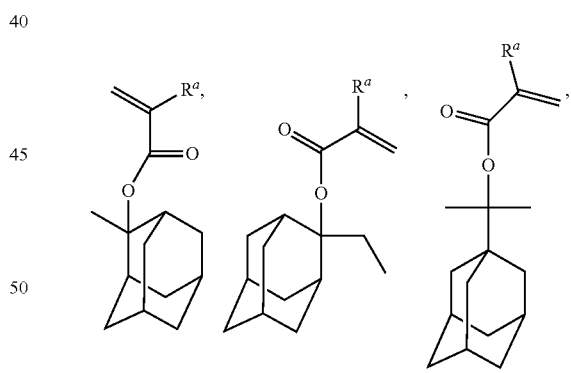

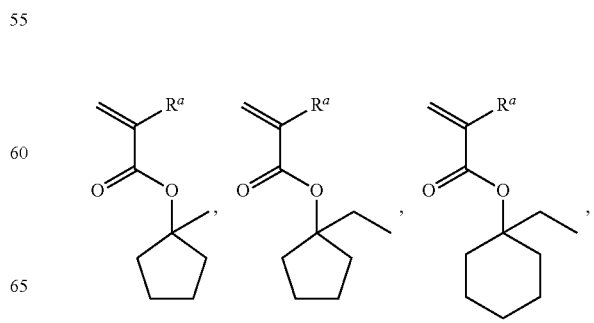

-continued

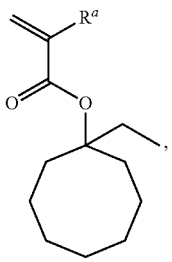

or a combination comprising at least one of the foregoing monomers, wherein $R^a$ is H, F, $C_{1-10}$ alkyl, or $C_{1-10}$ fluoroalkyl.

The polymer may also include other monomers, including cage-structured monomers for enhancing etch resistance, with or without functional groups for improving adhesion. An exemplary additional monomer may include:

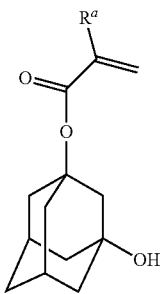

or a combination comprising the foregoing and at least one additional monomer, wherein $R^a$ is H, $C_{1-6}$ alkyl, or $CF_3$.

In addition, a photoresist is disclosed, which includes a polymer comprising the polymerized product of an acid-deprotectable monomer of Formula I, and an additional monomer copolymerizable with the acid-deprotectable monomer of Formula I as described herein; a photoacid generator; and optionally, a second acid sensitive polymer, and an amine or amide additive.

The second acid-sensitive polymer may be any polymer suitable for formulating photoresists for use at 193 nm. Such acid-sensitive polymers include an acid sensitive polymer comprising acid sensitive groups and lactone-containing groups, where the acid sensitive group deprotects a base-soluble group on exposure to acid.

The photoresist composition may further an amine or amide compound, referred to herein as a quencher. Quenchers may more broadly include, for example, those based on hydroxides, carboxylates, amines, imines, and amides. A useful quencher is an amine, an amide, or a combination comprising at least one of the foregoing. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as Troger's base, a hindered amine such as diazabicycloundecene (DBU) or diazabicyclononene (DBN), N-protected amines such as N-t-butylcarbonyl-1,1-bis(hydroxymethyl)-2-hydroxyethylamine (TBOC-TRIS), or ionic quenchers including quaternary alkyl ammonium salts such as tetrabutylammonium hydroxide (TBAH) or tetrabutyl ammonium lactate.

Other components of the photoresist may include solvents and surfactants.

Solvents generally suitable for dissolving, dispensing, and coating the components include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist composition disclosed herein may include the polymer in an amount of 50 to 99 wt %, specifically 55 to 95 wt %, more specifically 60 to 90 wt %, and still more specifically 65 to 90 based on the total weight of solids. It will be understood that "polymer" used in this context of a component in a photoresist may mean only the copolymer disclosed herein, or a combination of the polymer with another polymer useful in a photoresist. The photoacid generator may be present in the photoresist in an amount of 0.01 to 20 wt %, specifically 0.1 to 15 wt %, and still more specifically 0.2 to 10 wt %, based on the total weight of solids. A surfactant may be included in an amount of 0.01 to 5 wt %, specifically 0.1 to 4 wt %, and still more specifically 0.2 to 3 wt %, based on the total weight of solids. A quencher may be included in relatively small amounts of for example, from 0.03 to 5 wt % based on the total weight of solids. Other additives may be included in amounts of less than or equal to 30 wt %, specifically less than or equal to 20%, or more specifically less than or equal to 10%, based on the total weight of solids. The total solids content for the photoresist composition may be 0.5 to 50 wt %, specifically 1 to 45 wt %, more specifically 2 to 40 wt %, and still more specifically 5 to 35 wt %, based on the total weight of solids and solvent. It will be understood that the solids includes copolymer, photoacid generator, quencher, surfactant, and any optional additives, exclusive of solvent.

The photoresist disclosed herein may be used to form a film comprising the photoresist, where the film on the substrate constitutes a coated substrate. Such a coated substrate includes: (a) a substrate having one or more layers to be patterned on a surface thereof; and (b) a layer of the photoresist composition over the one or more layers to be patterned. Preferably, patterning is carried out using ultraviolet radiation at wavelength of less than 248 nm, and in particular, at 193 nm. In addition, a patternable film comprises a copolymer comprising the base soluble monomer of Formula I.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 200 mm, 300 mm, or larger in diameter, or other dimensions useful for wafer fabrication production.

The invention includes at least the following embodiments.

Embodiment 1

A monomer, having the Formula I:

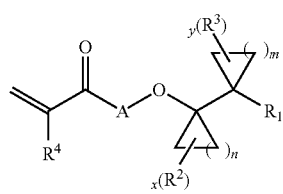

wherein $R^1$, $R^2$, and $R^3$ are each independently a $C_{1-30}$ monovalent organic group, and $R^1$, $R^2$, and $R^3$ are each independently unsubstituted or include a halogen, nitrile, ether, ester, ketone, alcohol, or a combination comprising at least one of the foregoing functional groups; $R^4$ includes H, F, $C_{1-4}$ alkyl, or $C_{1-4}$ fluoroalkyl; A is a single bond or a divalent linker group, wherein A is unsubstituted or substituted to include a halogen, nitrile, ether, ester, ketone, alcohol, or a combination comprising at least one of the foregoing functional groups; m and n are each independently an integer of 1 to 8; and x is 0 to 2n+2, and y is 0 to 2 m+2.

Embodiment 2

The monomer of claim 1, wherein $R^4$ is H, F, methyl, or trifluoromethyl.

Embodiment 3

The monomer of claim 1 or 2, wherein $R^1$, $R^2$, and $R^3$ are each independently $C_{1-10}$ alkyl, $C_{1-10}$ fluoroalkyl, $C_{1-10}$ alkoxy, $C_{1-10}$ fluoroalkoxy, $C_{1-10}$ alkanol, or a combination comprising at least one of the foregoing.

Embodiment 4

The monomer of claim 1 or 2, wherein $R^1$, $R^2$, and $R^3$ are each independently H, methyl, ethyl, trifluoromethyl, 2,2,2-trifluoroethyl, 2-hydroxyethyl, or a combination comprising at least one of the foregoing.

Embodiment 5

The monomer of any of claims 1-3, wherein m and n are independently 3 or 4, and x and y are independently an integer of from 0 to 2.

Embodiment 6

The monomer of any of claims 1-5, wherein $R^1$ is methyl or ethyl, m and n are each 3, and x and y are each 0.

Embodiment 7

The monomer of any of claims 1-6, wherein A is —O—CH$_2$(C=O)—.

Embodiment 8

A polymer, comprising the monomer of any of claims 1-7.

Embodiment 9

A photoresist composition, comprising the polymer of claim 8 and a photoacid generator.

Embodiment 10

A coated substrate, comprising: (a) a substrate having one or more layers to be patterned on a surface thereof; and (b) a layer of a photoresist composition of claim 9 over the one or more layers to be patterned.

Embodiment 11

A patterned layer, formed by patternwise imaging the coated substrate of claim 10 using actinic radiation at 193 nm.

The invention is further illustrated by the following examples. All compounds and reagents used herein are available commercially except where a procedure is provided below.

1'-methylcyclopentyl-1-cyclopentanol was prepared as described hereinbelow with respect to the reaction scheme shown in Reaction Scheme 2.

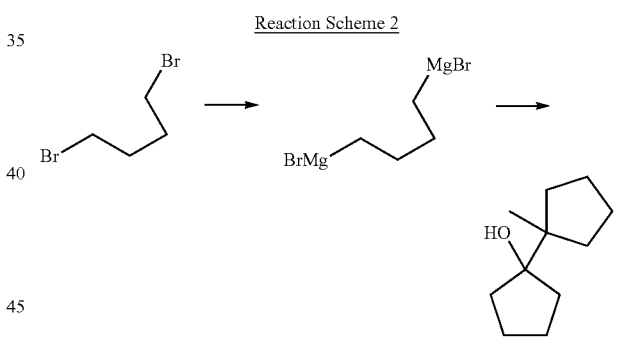

Reaction Scheme 2

Magnesium powder (60 g) was suspended in 0.5 L of tetrahydrofuran (THF). The mixture was heat to gentle reflux. A solution of 1,4-dibromobutane (246 g) in dry THF (1 L) was added dropwise over 6-8 hours. The mixture was maintained at gentle reflux for an additional 2 hour. A solution of ethyl 1-methyl-1-cyclopentanecarboxylate (156 g) in dry THF (0.3 L) was added dropwise to the above mixture over 4 hours. The mixture was stirred at reflux for an additional 2 hours and was cooled in ice bath. Saturated aqueous NH$_4$Cl solution (200 mL) was added dropwise to the stirring solution. The mixture was then filtered and the filtrate was washed with water twice and concentrated to give a colorless oil. Vacuum distillation of the oil afforded 1'-methylcyclopentyl-1-cyclopentanol (70% yield).

1'-methylcyclopentyl-1-cyclopentyl methacrylate was prepared as described hereinbelow with respect to the reaction scheme shown in Reaction Scheme 3.

Reaction Scheme 3

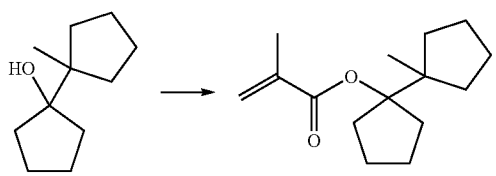

1'-Methylcyclopentyl-1-cyclopentanol (122 g) and triethylamine (183 g) were dissolved in dry $CH_2Cl_2$ (1 L). Methacryloyl chloride (151 g) was added dropwise. The mixture was stirred at 40° C. for 3 days. The reaction mixture was cooled in ice bath. Deionized water (500 mL) was added dropwise and the reaction mixture was stirred for an additional 15 minutes, at which time the upper aqueous phase and the lower organic phase were separated. The organic layer was washed with water (1×100 mL), HCl (0.3N, 2×100 mL), $NaHCO_3$ (2×100 mL) successively, dried with $Na_2SO_4$, and concentrated to give a pale yellow oil. Vacuum distillation of the oil gave 1'-methylcyclopentyl-1-cyclopentyl methacrylate (monomer A) in 35% yield.

The sodium difluorosulfoacetate ester of 3-oxo-4,10-dioxa-tricyclo[5.2.1.02,6]decan-8(or 9)-ol was prepared by the following procedure shown in Reaction Scheme 4.

Reaction Scheme 4

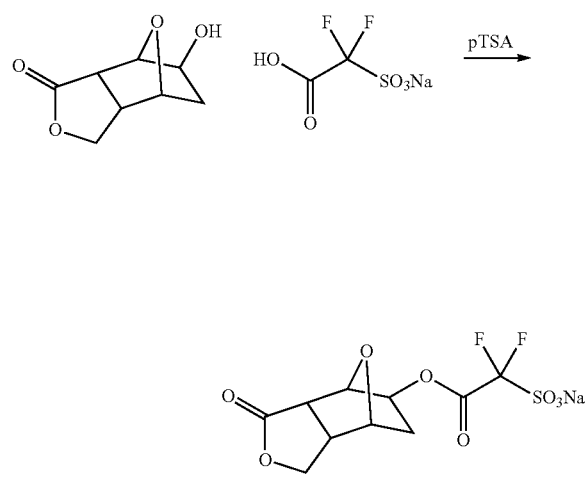

A mixture of sodium difluorosulfoacetate (5 g), 3-oxo-4,10-dioxa-tricyclo[5.2.1.02,6]decan-8(or 9)-ol (4.21 g) and pTSA (9.5 g) in toluene (50 mL) was refluxed for 3 days. The reaction mixture was cooled to room temperature and filtered. The solids were extracted with $CH_3CN$ (2×50 mL) and filtered. The $CH_3CN$ filtrate was concentrated to dryness. The residue was partitioned between water (50 mL) and $CH_2Cl_2$ (30 mL). The upper aqueous phase, and lower organic phase were separated. The aqueous phase was washed with additional $CH_2Cl_2$ (2×30 mL), and the aqueous phase containing the sodium difluorosulfonate ester salt was used in the next step without further purification.

The triphenylsulfonium salt of the difluorosulfonate acetate ester of 3-oxo-4,10-dioxa-tricyclo[5.2.1.02,6]decan-8(or 9)-ol was prepared by the following procedure shown in Reaction Scheme 5.

Reaction Scheme 5

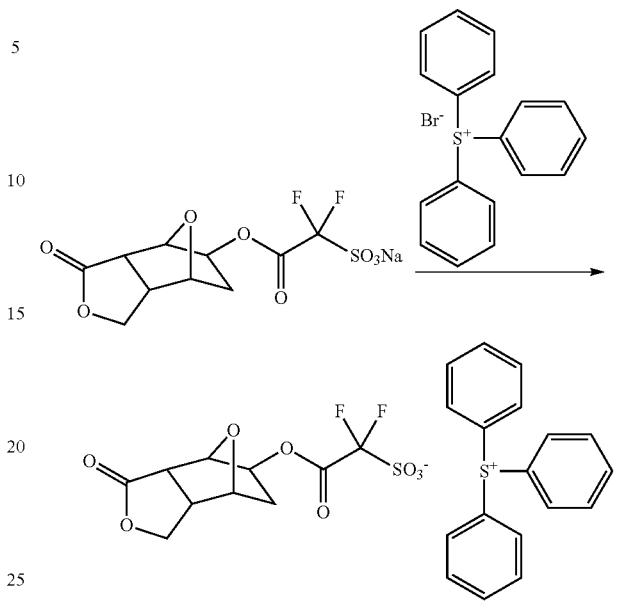

The aqueous solution of the sodium difluorosulfonate ester was treated with TPS-Br (8.6 g) and $CH_2Cl_2$ (50 mL). The mixture was stirred at room temperature for 24 hours. Phases were separated. The organic phase was washed with water (3×30 mL), dried with $Na_2SO_4$, and concentrated. The residue was purified by column chromatography ($SiO_2$, 3% MeOH in $CH_2Cl_2$) to give the triphenylsulfonium salt of the difluorosulfonate acetate ester of 3-oxo-4,10-dioxa-tricyclo [5.2.1.02,6]decan-8(or 9)-ol (PAG 1; 7.5 g) as a white solid.

Polymers used in the examples were prepared by the following methods. Monomers used in the preparation of these polymers were obtained commercially. The monomers are shown below and include (B) adamantyl isopropyl methacrylate (TAM); (C) alpha-gamma butyrolactone methacrylate (α-GBLMA); (D) 3-oxo-4,10-dioxa-tricyclo[5.2.1.0.2,6] dec-8(or 9)-yl methacrylate (ODOTMA); (E) 3-hydroxyadamantan-1-yl methacrylate (HAMA). Weight average molecular weight (Mw) and polydispersity (Mw/Mn) of the polymers were determined by gel permeation chromatography (GPC) using a sample concentration of 1 mg/ml and a crosslinked styrene-divinylbenzene column with universal calibration curve calibrated with polystyrene standards, and eluted with tetrahydrofuran at a flow rate of 1 ml/min.

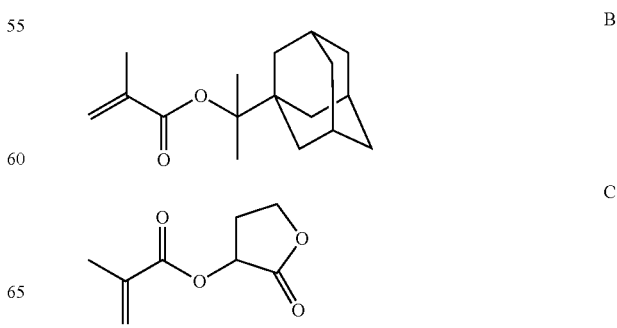

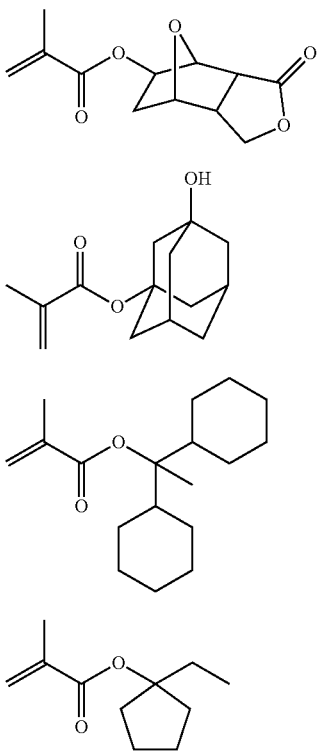

Polymer 1 (A/C/D/E, molar ratio 40/30/20/10) was prepared by the following procedure. Monomer A (15.3 g), monomer B (8.2 g), monomer C (7.7 g), and monomer D (3.8 g) were dissolved in tetrahydrofuran (~70 mL) and degassed with bubbled nitrogen. A solution of dimethyl-2,2-azo(bis) diisobutyrate initiator (VAZO V-601, available from DuPont) in tetrahydrofuran was weighed into a separate flask and degassed with bubbled nitrogen. The flask containing this initiator solution was heated to 70° C., and the monomer solution was then fed into the initiator solution over 3.5 hours then held at temperature for 30 minutes. Additional tetrahydrofuran (~70 mL) was then added and the solution was allowed to cool to room temperature. The solution was then precipitated into 20 volumes of isopropyl alcohol, the resulting precipitated polymer collected by filtration, dried, redissolved in tetrahydrofuran to approximately 30% w/w concentration and reprecipitated in a second 20 volumes of isopropyl alcohol. The polymer was then dried overnight at 45° C. under vacuum to yield the target polymer (83%). Mw=10285; Mw/Mn=1.62.

Polymer 2 (B/C/D/E, molar ratio 40/30/20/10) was prepared by the following procedure. Monomer B (16.2 g), monomer B (7.9 g), monomer C (7.3 g), and monomer D (3.6 g) were dissolved in tetrahydrofuran (~70 mL) and degassed with bubbled nitrogen. A solution of dimethyl-2,2-azo(bis) diisobutyrate initiator (VAZO V-601, available from DuPont) in tetrahydrofuran was weighed into a separate flask and degassed with bubbled nitrogen. The flask containing initiator solution was heated to 70° C., and the monomer solution was then fed into the initiator solution over 3.5 hours then held at temperature for 30 minutes. Additional tetrahydrofuran (~70 mL) was then added and the solution allowed to cool to room temperature. The solution was then precipitated into 20 volumes of isopropyl alcohol, the resulting precipitated polymer collected by filtration, dried, redissolved in tetrahydrofuran to approximately 30% w/w concentration and reprecipitated in a second 20 volumes of isopropyl alcohol. The polymer was then dried overnight at 45° C. under vacuum to yield the target polymer (83%). Mw=6685; Mw/Mn=1.46.

Polymer 3 (F/C/D/E, molar ratio 40/30/20/10) was prepared by the following procedure. Monomer B (16.2 g), monomer B (7.9 g), monomer C (7.3 g), and monomer D (3.6 g) were dissolved in tetrahydrofuran (~70 mL) and degassed with bubbled nitrogen. A solution of dimethyl-2,2-azo(bis) diisobutyrate initiator (VAZO V-601, available from DuPont) in tetrahydrofuran was weighed into a separate flask and degassed with bubbled nitrogen. The flask containing initiator solution was heated to 70° C., and the monomer solution was then fed into the initiator solution over 3.5 hours then held at temperature for 30 minutes. Additional tetrahydrofuran (~70 mL) was then added and the solution allowed to cool to room temperature. The solution was then precipitated into 20 volumes of isopropyl alcohol, the resulting precipitated polymer collected by filtration, dried, redissolved in tetrahydrofuran to approximately 30% w/w concentration and reprecipitated in a second 20 volumes of isopropyl alcohol. The polymer was then dried overnight at 45° C. under vacuum to yield the target polymer (83%). Mw=9492; Mw/Mn=1.49.

Polymer 4 (G/C/D/E, molar ratio 40/30/20/10) was prepared by the following procedure. Monomer B (11.1 g), monomer B (7.9 g), monomer C (7.3 g), and monomer D (3.6 g) were dissolved in tetrahydrofuran (~70 mL) and degassed with bubbled nitrogen. A solution of dimethyl-2,2-azo(bis) diisobutyrate initiator (VAZO V-601, available from DuPont) in tetrahydrofuran was weighed into a separate flask and degassed with bubbled nitrogen. The flask containing initiator solution was heated to 70° C., and the monomer solution was then fed into the initiator solution over 3.5 hours then held at temperature for 30 minutes. Additional tetrahydrofuran was then added and the solution cooled to room temperature. The solution was then precipitated into 20 volumes of isopropyl alcohol, the resulting precipitated polymer collected by filtration, dried, redissolved in tetrahydrofuran to approximately 30% w/w concentration and reprecipitated in a second 20 volumes of isopropyl alcohol. The polymer was then dried overnight at 45° C. under vacuum to yield the target polymer (83%). Mw=6662; Mw/Mn=1.42.

The relative deprotection half life for each of the polymers, and hence for monomers A (Polymer 1), monomer B (Polymer 2), monomer F (Polymer 3) and monomer G (Polymer 4) were determined as follows. DMSO-$d_6$ solutions containing 5 wt % of monomer and equal molar methanesulfonic acid were prepared. Disappearance of monomers A, B, F and G in acidic DMSO-$d_6$ at 80° C. was monitored via $^1$H-NMR. The rate constants were obtained as the slope of Ln(monomer concentration) vs time. Deprotection half lives were calculated from Ln(2) over rate constant, where Ln(2) derives from the rate equation (equation 1):

Ln([initial concentration]/[half concentration])=Ln(2)  (equation 1).

The relative deprotection half lives are shown in Table 1, below.

TABLE 1

| Example | Relative Deprotection Half Life |
|---------|--------------------------------|
| A | 1 |
| B | 16.1 |
| F | <1 |
| G | 19.5 |

As seen in Table 1, the relative deprotection half life for monomers B (Polymer 2), and G (Polymer 4) are significantly greater (>16× greater) than for monomers A (Polymer 1; the exemplary polymer) and monomer F (Polymer 3). Monomers A and F each have structures which provide for a statistically greater probability for elimination of hydrogen to form the product alkene at tertiary or secondary centers, whereas monomers B and G each have structure which generate more strained or sterically less favored elimination products.

The Ohnishi Parameter was determined to approximate the relative etch rate for these monomers, using the following equation 2:

$$N/(N_c - N_o) = \text{Ohnishi parameter} \quad \text{(equation 2)}$$

where N, $N_c$ and $N_o$ are the total number of atoms, number of carbon atoms, and number of oxygen atoms, respectively, per monomer. The results are provided in Table 2, below.

The Ring Parameter was also determined for each of monomers A, B, F, and G (Polymers 1-4, respectively), where this parameter is defined as $M_{cr}/M_{tot}$, where $M_{cr}$ and $M_{tot}$ are the mass of the polymer existing as carbon atoms contained in a ring structure and the total polymer mass, respectively. Ohnishi and Ring parameters are shown in Table 2, below.

TABLE 2

|  | Ohnishi | Ring |
| --- | --- | --- |
| polymer 1 | 4.13 | 0.42 |
| polymer 2 | 4.07 | 0.40 |
| polymer 3 | 4.12 | 0.42 |
| polymer 4 | 4.25 | 0.35 |

As seen in Table 2, the Ohnishi parameter for Polymer 4 (monomer G) is highest indicating low etch rate, though the ring parameter is lowest. Polymer 2 (monomer B) has the lowest Ohnishi parameter and intermediate Ring parameter. However, Polymer 1 (monomer A, the exemplary monomer) and Polymer 3 (monomer F) each exhibit comparable Ohnishi and Ring parameters, indicating better etch than Polymer 2 and at least comparable etch to Polymer 4.

The photoresists were formulated using the components and proportions shown in Table 3, below. Note that the base (N-t-butyloxycarbonyl-tris(hydroxymethylmethylamine, TB-tris), available from TCI, and surface leveling agent (SLA; also referred to as surfactant) PF 656, available from Omnova, are each provided below as weight percent based on 100% solids content, with the balance of the solids being the polymer. The proportions of solvents (propylene glycol methyl ether acetate, PGMEA; methyl 2-hydroxybutyrate, HBM; and cyclohexanone, CH) are based on the total solvent weight; the final % solids is after dilution of the solids with the combined solvents, and filtering using a 0.1 µm filter.

TABLE 3

| Example | Polymer | PAG | Base | PGMEA (w/w of solvent) | HBM (w/w of solvent) | CH (w/w of solvent) | % solids |
| --- | --- | --- | --- | --- | --- | --- | --- |
| Ex. 1 | Polymer 1 (100) | PAG1 (13%) | TB-tris (1.6%) | 30 | 50 | 20 | 3.8 |
| CEx. 1 | Polymer 2 (100) | PAG1 (13%) | TB-tris (1.6%) | 30 | 50 | 20 | 3.8 |
| CEx. 2 | Polymer 3 (100) | PAG1 (13%) | TB-tris (1.6%) | 30 | 50 | 20 | 3.8 |
| CEx. 3 | Polymer 4 (100) | PAG1 (13%) | TB-tris (1.6%) | 30 | 50 | 20 | 3.8 |

Lithographic evaluation was carried out as follows. The formulated photoresists were spin coated using a TEL Clean Track™ Lithius-i+™ (Tokyo Electron) coating track onto a 300 mm silicon wafer having sequentially applied first and second bottom antireflective coatings (BARC) (respectively, AR™124 and AR™26N, Dow Electronic Materials), and soft baked at 100° C. for 60 seconds, to form a resist film of about 90 nm in thickness. A top coat OC™2000 was applied onto the resist film and baked at 90° C. for 60 seconds. The photoresist layer was exposed using a TwinScan™ XT: 1900i, 1.35 NA stepper (ASML) operating at 193 nm through a photomask with 008LSBIN1900i 40 nm space/78 pitch Trench. The exposed wafers were post-exposed baked (PEB) at 95° C. for 60 seconds. The exposed wafers were next treated with a metal ion free base developer (0.26N aqueous tetramethylammonium hydroxide solution) to develop the exposed photoresist layer. Sizing dose was defined as an exposure energy to print the target by varying exposure energy. Exposure latitude (EL) was defined as a difference in exposure energy to print +/−10% of the target CD normalized by the sizing energy. Depth of focus (DOF) was determined by a defocus range that gives +/−10% of the target CD. LWR was calculated from a standard deviation of 300 measured CD at the best focus and at the sizing energy.

The lithographic results for linewidth roughness (LWR) are summarized in Table 4, below.

TABLE 4

| Photoresist Example | LWR |
| --- | --- |
| Ex. 1 | 3.5 |
| CEx. 1 | Too slow at 100° C. PEB |
| CEx. 2 | 3.8 |
| CEx. 3 | 3.4 |

As shown in Table 4, of the comparative examples, CEx. 1 exhibited too slow a photospeed when processed at a post exposure bake of 100° C. and did not clear. Example 1 showed improved LWR over Comparative Example 2, and approximately comparable LWR when compared with Comparative Example 3.

To summarize the data, Example 1 (monomer A) shows significantly improved deprotection half life and predicted etch (based on Ohnishi and Ring parameters) over monomers B and G (polymers 2 and 4, used in CEx. 1 and CEx. 3, respectively), and improved LWR over monomer F (polymer 3, in CEx. 2). Hence, monomer A provides a balance of properties when incorporated in a polymer and photoresist, which is not obtained with the comparative monomers B, F, and G.

All ranges disclosed herein are inclusive of the endpoints, and the endpoints are independently combinable with each other. The suffix "(s)" as used herein is intended to include both the singular and the plural of the term that it modifies, thereby including at least one of that term. "Optional" or "optionally" means that the subsequently described event or circumstance can or cannot occur, and that the description includes instances where the event occurs and instances where it does not. As used herein, "combination" is inclusive of blends, mixtures, alloys, or reaction products. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another.

The invention claimed is:

1. A monomer, having the Formula I:

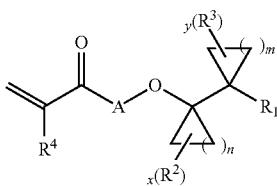

wherein $R^1$, $R^2$, and $R^3$ are each independently a $C_{1-30}$ monovalent organic group, and $R^1$, $R^2$, and $R^3$ are each independently unsubstituted or include a halogen, nitrile, ether, ester, ketone, alcohol, or a combination comprising at least one of the foregoing functional groups;
$R^4$ includes H, F, $C_{1-4}$ alkyl, or $C_{1-4}$ fluoroalkyl;
A is a single bond or a divalent linker group, wherein A is unsubstituted or substituted to include a halogen, nitrile, ether, ester, ketone, alcohol, or a combination comprising at least one of the foregoing functional groups;
m is 3, and n is an integer of 1 to 8; and
x is 1 to 2n+2, and y is 0 to 2m+2.

2. The monomer of claim 1, wherein $R^4$ is H, F, methyl, or trifluoromethyl.

3. The monomer of claim 1, wherein $R^1$, $R^2$, and $R^3$ are each independently $C_{1-10}$ alkyl, $C_{1-10}$ fluoroalkyl, $C_{1-10}$ alkoxy, $C_{1-10}$ fluoroalkoxy, $C_{1-10}$ alkanol, or a combination comprising at least one of the foregoing.

4. The monomer of claim 1, wherein $R^1$, $R^2$, and $R^3$ are each independently methyl, ethyl, trifluoromethyl, 2,2,2-trifluoroethyl, 2-hydroxyethyl, or a combination comprising at least one of the foregoing.

5. The monomer of claim 1, wherein n is 3 or 4, x is 1 or 2, and y is an integer of from 0 to 2.

6. The monomer of claim 1, wherein $R^1$ is methyl or ethyl, n is 3, and y is 0.

7. A polymer, comprising the monomer of claim 1.

8. A photoresist composition, comprising the polymer of claim 7 and a photoacid generator.

9. A coated substrate, comprising: (a) a substrate having one or more layers to be patterned on a surface thereof; and (b) a layer of a photoresist composition of claim 8 over the one or more layers to be patterned.

10. A patterned layer, formed by patternwise imaging the coated substrate of claim 9 using actinic radiation at 193 nm.

11. A monomer, having the Formula I:

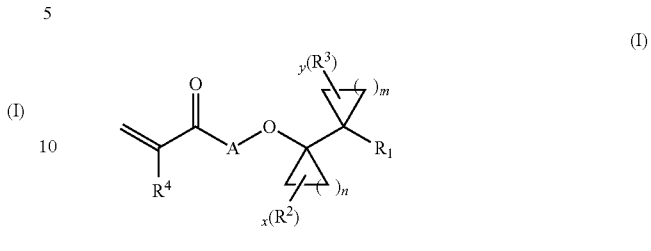

wherein $R^1$, $R^2$, and $R^3$ are each independently a $C_{1-30}$ monovalent organic group, and $R^1$, $R^2$, and $R^3$ are each independently unsubstituted or include a halogen, nitrile, ether, ester, ketone, alcohol, or a combination comprising at least one of the foregoing functional groups;
$R^4$ includes H, F, $C_{1-4}$ alkyl, or $C_{1-4}$ fluoro alkyl;
A is $-O-CH_2(C=O)-$;
m and n are each independently an integer of 1 to 8; and
x is 0 to 2n+2, and y is 0 to 2m+2.

12. The monomer of claim 11, wherein $R^4$ is H, F, methyl, or trifluoromethyl.

13. The monomer of claim 11, wherein $R^1$, $R^2$, and $R^3$ are each independently $C_{1-10}$ alkyl, $C_{1-10}$ fluoroalkyl, $C_{1-10}$ alkoxy, $C_{1-10}$ fluoroalkoxy, $C_{1-10}$ alkanol, or a combination comprising at least one of the foregoing.

14. The monomer of claim 11, wherein $R^1$, $R^2$, and $R^3$ are each independently methyl, ethyl, trifluoromethyl, 2,2,2-trifluoroethyl, 2-hydroxyethyl, or a combination comprising at least one of the foregoing.

15. The monomer of claim 11, wherein m and n are independently 3 or 4, and x and y are independently an integer of from 0 to 2.

16. The monomer of claim 11, wherein $R^1$ is methyl or ethyl, m and n are each 3, and x and y are each 0.

17. A polymer, comprising the monomer of claim 11.

18. A photoresist composition, comprising the polymer of claim 17 and a photoacid generator.

19. A coated substrate, comprising: (a) a substrate having one or more layers to be patterned on a surface thereof; and (b) a layer of a photoresist composition of claim 18 over the one or more layers to be patterned.

20. A patterned layer, formed by patternwise imaging the coated substrate of claim 19 using actinic radiation at 193 nm.

* * * * *